United States Patent
O'Connor

(10) Patent No.: US 6,398,792 B1
(45) Date of Patent: Jun. 4, 2002

(54) ANGIOPLASTY CATHETER WITH TRANSDUCER USING BALLOON FOR FOCUSING OF ULTRASONIC ENERGY AND METHOD FOR USE

(76) Inventor: Lawrence O'Connor, 1636 Virginia Ave., Glendale, CA (US) 91202

(*) Notice: Subject to any disclaimer, the term of this patent is extended or adjusted under 35 U.S.C. 154(b) by 0 days.

(21) Appl. No.: 09/342,159

(22) Filed: Jun. 21, 1999

(51) Int. Cl.⁷ .............................................. A61B 17/22
(52) U.S. Cl. .................. 606/128; 600/470; 604/101.01
(58) Field of Search .................. 606/191, 192, 606/194, 200, 157, 169, 128; 604/22, 101.01, 101.03; 600/439, 443, 454, 459, 466, 470, 471

(56) References Cited

U.S. PATENT DOCUMENTS

| | | | |
|---|---|---|---|
| 4,425,908 A | * 1/1984 | Simon | 128/1 |
| 5,009,232 A | * 4/1991 | Hassler et al. | 128/660.03 |
| 5,059,178 A | * 10/1991 | Ya | 604/101 |
| 5,197,978 A | * 3/1993 | Hess | 623/1 |
| 5,222,941 A | 6/1993 | Don Michael | |
| 5,267,954 A | * 12/1993 | Nita | 604/22 |
| 5,269,291 A | * 12/1993 | Carter | 128/24 |
| 5,279,546 A | * 1/1994 | Nische et al. | 604/22 |
| 5,304,115 A | * 4/1994 | Pflueger et al. | 604/22 |
| 5,312,328 A | * 5/1994 | Nita et al. | 604/22 |
| 5,318,014 A | * 6/1994 | Carter | 601/2 |
| 5,324,255 A | * 6/1994 | Passafaro et al. | 604/22 |
| 5,326,342 A | * 7/1994 | Pfueger et al. | 604/22 |
| 5,342,292 A | * 8/1994 | Nita et al. | 604/22 |
| 5,368,557 A | * 11/1994 | Nita et al. | 604/22 |
| 5,421,338 A | * 6/1995 | Crowley et al. | 128/662.06 |
| 5,431,663 A | * 7/1995 | Carter | 606/128 |
| 5,540,656 A | * 7/1996 | Pflueger et al. | 604/22 |
| 5,558,092 A | * 9/1996 | Unger et al. | 128/660.03 |
| 5,571,086 A | 11/1996 | Kaplan et al. | |
| 5,609,606 A | * 3/1997 | O'Boyle | 606/194 |
| 5,616,114 A | 4/1997 | Thornton et al. | |
| 5,695,519 A | 12/1997 | Summers et al. | |
| 5,810,748 A | * 9/1998 | Ueberle | 601/4 |
| 5,846,218 A | 12/1998 | Brisken et al. | |
| 5,876,344 A | * 3/1999 | Baker et al. | 600/463 |
| 5,941,896 A | * 8/1999 | Kerr | 606/200 |
| 5,957,882 A | * 9/1999 | Nita et al. | 604/22 |
| 5,971,955 A | * 10/1999 | Nap et al. | 604/101 |
| 6,004,269 A | * 12/1999 | Crowley et al. | 600/439 |
| 6,007,514 A | * 12/1999 | Nita | 604/22 |
| 6,264,608 B1 | * 7/2001 | Schatzle et al. | 600/439 |

* cited by examiner

Primary Examiner—Jeffrey A. Smith
Assistant Examiner—Michael B. Priddy
(74) Attorney, Agent, or Firm—John E. Wagner; Robert C. Smith

(57) ABSTRACT

A catheter for insertion into an artery having deposits of plaque and/or thrombus includes, at its distal end an ultrasonic transducer and a dilatation balloon surrounding the transducer such that when the balloon is positioned in the artery adjacent the deposits and inflated, energizing of the ultrasonic transducer will focus the ultrasonic energy against the deposits to cause dissolution of the thrombus into microscopic particles and cause cracking and softening of the plaque. Other embodiments include the provision of a second ultrasonic transducer as a means for viewing the treatment site, and a second balloon to cooperate with the first balloon to define a chamber between the balloons and with a lumen and a port connected to the chamber to remove any debris of larger than microscopic size which might otherwise tend to move downstream and cause further obstructions. Also described is the use of an expandable filtering device distal of the dilatation balloon for trapping such particles. Subsequently to the ultrasonic radiation of the deposits the dilatation balloon can be further inflated to force a stent into the wall of the artery.

6 Claims, 2 Drawing Sheets

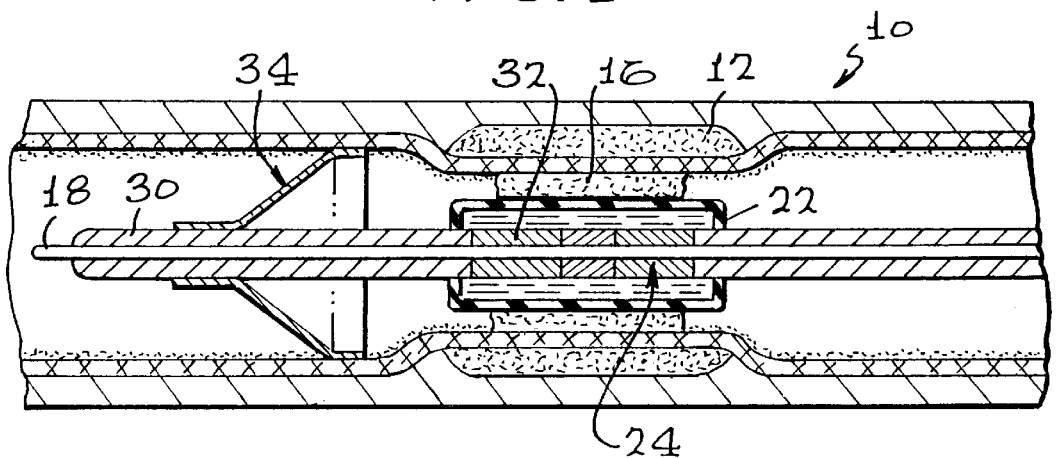
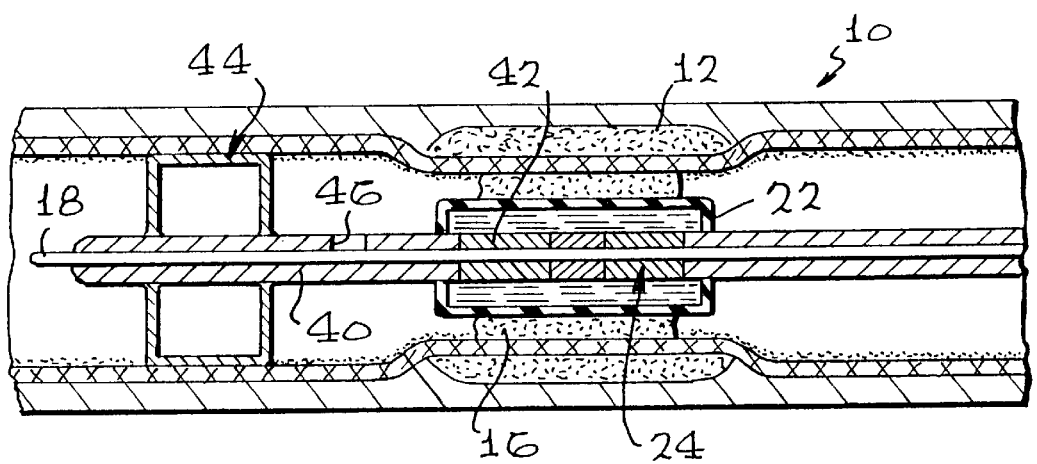
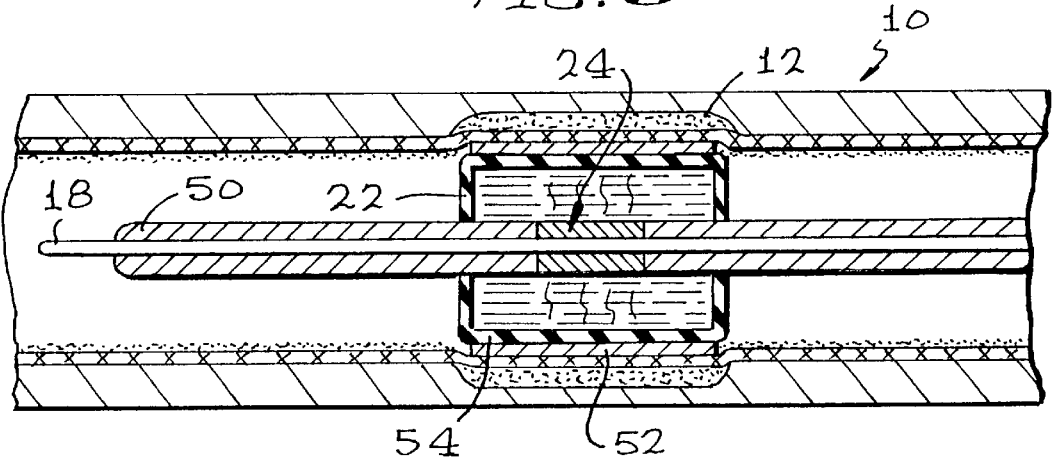

ANGIOPLASTY CATHETER WITH TRANSDUCER USING BALLOON FOR FOCUSING OF ULTRASONIC ENERGY AND METHOD FOR USE

BACKGROUND OF THE INVENTION

This invention relates to an ultrasonic angioplasty device for insertion into arteries for treating of obstructions caused by plaque and thrombi and more particularly to a vascular catheter which combines balloon dilatation capabilities with ablation through ultrasonic treatment of such obstructions.

One of the obstructions encountered in percutaneous transluminal angioplasty is thrombus or a blood clot which develops within the artery and the other is plaque which is present in the wall of the artery. Occasionally during balloon angioplasty the migration of large particles of thrombus material or plaque results either in damage to the blood vessel wall or movement of loose material into the blood vessel lumen causing reclosure or closure of other vessels. Similarly, it is sometimes difficult to dispel a large thrombus burden.

There have been a number of patents dealing either with the balloon angioplasty in combination with ultrasonic imaging means or with balloon angioplasty combined with removal of plaque and/or thrombi.

U.S. Pat. No. 4,924,863 to Sterzer describes a method of removing plaque using two juxtaposed catheters in a vas. At the distal end of one catheter is a balloon which is inflated asymnetrically so that it presses against one side of the vas. The other catheter includes a heating element which, when the balloon is inflated presses the heating element against the region of plaque to be treated. Just enough heat is applied through microwave or radio frequency energy to cause some melting of the fatty plaque deposit. Suction is then applied to the second catheter to pull the liquefied plaque material out from the proximal end of the catheter. Where the plaque has become calcified, an ultrasonic transducer is substituted for the heating element and is employed to ablate material from the surface of the plaque deposit and the ablated material is removed by suction applied to the proximal end of the second catheter.

U.S. Pat. No. 5,195,955 to Don Michael shows a catheter in an artery obstructed by plaque and/or thrombus. The catheter includes a balloon designed to inflate asymmetrically, but to seal off the artery except for limited flow through one lumen of the catheter. Ports are supplied on opposite sides of the inflated balloon which permit limited flow of blood through the lumen, but the balloon seals off the artery so that debris from a separate procedure operating proximally of the balloon to remove the obstruction does not flow downstream. A separate lumen is described for applying suction to remove the debris.

U.S. Pat. No. 5,118,831 to Yue-Teh Feng et al shows a vascular catheter with tandem imaging and dilatation components located in its distal end. Separate lumens within the catheter permit different fluids to be used for inflating the balloon and for ultrasonic imaging. A rotatable cable drives a rotatable scanning mirror which receives sonic signals from an adjacent transducer. This patent describes a straightforward angioplasty procedure enhanced by the use of an ultrasonic scanning device in the same catheter.

A recent article in *The Journal of Invasive Cardiology*, Vol. 10/Supplement A dated Mar. 10, 1998 entitled "Mechanical Thrombectomy in Acute Ischemic Syndromes: Cufters, Suckers, and Busters" by Jeffrey W. Moses M. D. deals with many of the above problems and with methods and apparatus for dealing with such problems.

It seems clear that although many techniques have been devised for dealing with the problems discussed above, none are universally useful. While one method or technique may be helpful in one situation, it may not help in another. In particular there is a need for a device or apparatus which can remove or substantially ameliorate plaque and thrombi deposits while minimizing the danger from migration of large particles of debris.

SUMMARY OF THE INVENTION

A unique feature of the present invention is the mounting of an ultrasonic device on the distal end of the catheter inside the span of the balloon on the catheter so that the balloon, when inflated, can focus and deliver ultrasound energy to two pathologic sites within the artery, i.e., the thrombus and the plaque sites. By focusing or concentrating ultrasound energy to the thrombus and the plaque deposits, the thrombus can be caused to disintegrate into microscopic sized particles which can pass into the circulatory system without damage to other vessels downstream. At the same time, or during the same procedure, the concentrated ultrasonic energy tends to fracture and thereby soften plaque deposits.

Depending upon the nature of the obstruction, the cardiologist may be concerned that larger sized thrombus particles or plaque particles may escape downstream and cause blockage of additional vessels. Applicant has devised a catheter arrangement utilizing a second balloon on the catheter distal of the first balloon thereby defining a chamber within the artery and between the balloons into which any such larger particles are contained. A port in the catheter wall communicates with this chamber and is connected to a source of negative pressure for drawing the debris from the chamber and out the proximal end of the catheter.

Another embodiment of this invention utilizes an expandable umbrella-like element carried on the catheter downstream of the balloon and the ultrasonic transducer. This device, which may constitute a filter capable of passing normal blood, is expanded at the time the ultrasonic transducer is energized to trap any larger particles, preventing them from moving downstream. At the end of the procedure, the umbrella-like element is collapsed around the larger particles which are then removed along with the catheter.

BRIEF DESCRIPTION OF THE DRAWINGS

This invention may be more clearly understood with the following detailed description and by reference to the drawings in which:

FIG. 4 is a cross-sectional view of the artery of FIGS. 1–3 showing another embodiment of the invention;

FIG. 5 is a cross-sectional view similar to FIG. 4 showing an additional embodiment of the invention; and FIG. 6 is a cross-sectional view similar to that of FIG. 1 in which the obstruction is only plaque.

DETAILED DESCRIPTION OF THE INVENTION

Figure 1:
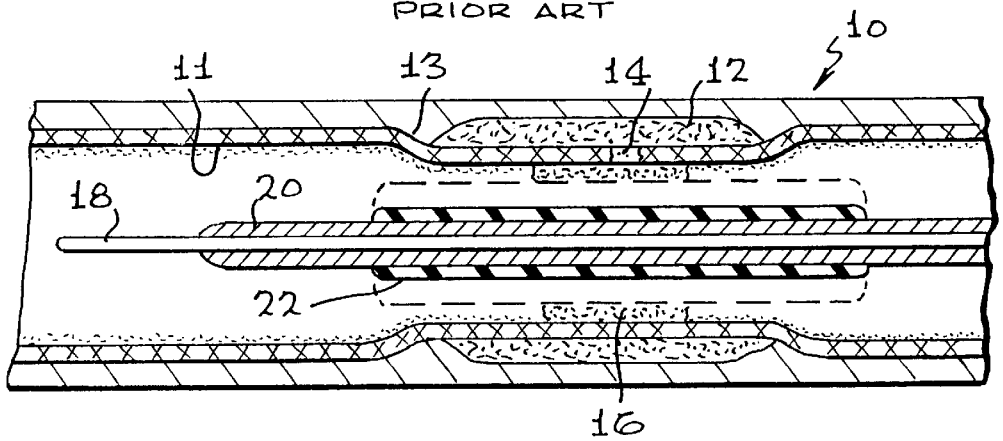
FIG. 1 is a cross-sectional view of an artery substantially blocked by plaque and thrombus.

Referring to FIG. 1, there is shown a portion of the length of an artery 10 such as a coronary artery. The lumen of artery 10 is partially occluded by artherosclertic plaque 12 embedded in the wall of artery 10 between the inner layer or intima 11 and the central layer or media 13. Because of the presence of calcified plaque 12 a crack or ulceration 14 has occurred in the intima 11 resulting in a blood clot or thrombus 16 which has substantially blocked flow through artery 10. Inserted through thrombus 16 is a guide wire 18 and a catheter 20 carrying a balloon 22. This represents a typical prior art balloon angioplasty arrangement in which the balloon, when inflated as shown by the dashed lines, significantly opens the occluded part of the artery by pressing the thrombus against the internal wall of artery 10.

While the above procedure is often successful, at least for a time, problems frequently occur because the procedure may result in creation of large aggregates of thrombus material which float downstream, block capillaries, reduce flow and produce some degree of micro-infarction. As a result, patients may develop ventricular tachycardia, accelerated idioventricular rhythm or complete heart block. While these problems are currently dealt with through the use of 23B platelet inhibitors, this is associated with a risk of bleeding.

Figure 2:
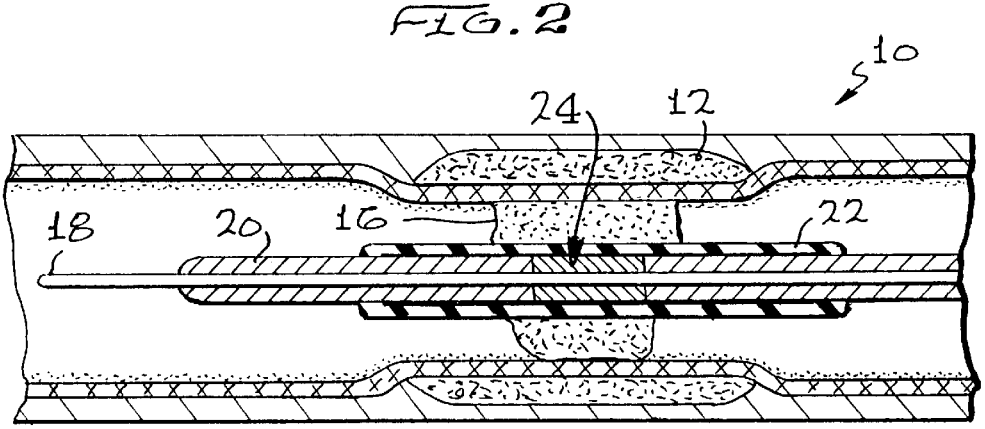
FIG. 2 is a cross-sectional view of the artery of FIG. 1 with a balloon catheter placed in the artery and an ultrasound transducer within the balloon.
Figure 3:
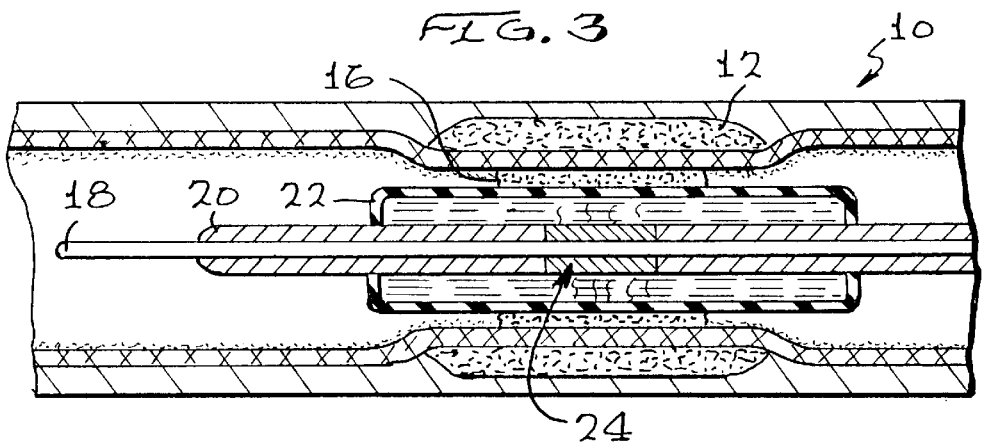
FIG. 3 is a cross-sectional view of the artery of FIGS. 1 and 2 with the balloon inflated at low pressure.

Applicant's device and method minimizes the above risks by using the balloon to trap the thrombus and to serve as a focusing device and coupling device to efficiently deliver ultrasonic energy into the thrombus. Referring now to FIG. 2, the catheter 20 carrying a balloon 22 at its distal end is inserted into artery 10 and through thrombus 16 along guide wire 18. Catheter 20 will typically carry a plurality (such as three) internal lumens to inflate the balloon, to slide over a guidewire and to carry wires for electrical energy or imaging. These have not been shown to avoid unnecessarily confusing the drawings. Carried on catheter 20 is an ultrasonic transducer 24 (typically a piezoelectric member) connected to an ultrasonic signal source (not shown) adjacent the proximal end of catheter 20. With the catheter 20, balloon 22 and transducer 24 positioned within artery 10 as shown, the balloon 22 is inflated to a moderate pressure (1 to 3 atmospheres) through injection of an aqueous solution containing a contrast agent as an aid in viewing the process as shown in FIG. 3. The balloon 22 thus presses against or traps the thrombus 16 against the inner layer or intema 11 of artery 10. Following inflation of the balloon 20, the ultrasonic transducer 24 is energized causing ultrasonic energy to pass through the inflated balloon to the thrombus 16. The aqueous solution in the balloon 22 readily transmits and focuses energy to the thrombus which breaks up the thrombus into microparticulate matter with particles as small as 8 to 10 microns. This matter can then flow through the patient's system without producing any of the adverse effects referred to above including no flow or slow flow.

The ultrasonic energy from transducer 23 also creates microfractures within the calcified plaque 12 which is embedded in the wall of artery 10. This leaves the plaque 12 softer and in better condition to be dealt with by other interventional modalities such as mechanical ablation or intracoronary stent.

Depending upon tile nature of the plaque 12 and the thrombus material 16 the cardiologist may have concerns that either plaque particles or thrombus particles of significantly larger size than the microscopic particles referred to above may tend to flow downstream of the obstruction following the ultrasonic radiation process referred to above. In such case, a catheter arrangement like that of FIGS. 4 or 5 may be used. In FIG. 4, a catheter 30 is inserted over guide wire 18 into an artery 10 occluded by plaque deposits 12 and thrombus 16. In additional to balloon 22 and ultrasonic transducer 24, catheter 30 also carries a second ultrasonic transducer 32 used as an imaging device for assisting the cardiologist in observing the obstruction and the results of the ultrasonic radiation process. A collapsible and expandable umbrella-like shield 34 is positioned a short distance distally of the transducer 32 and is shown in opened configuration where it blocks the passage farther downstream of larger particles of plaque or thrombus material. Shield 34 may act as a filter passing normal blood components but blocking larger particles. Following completion of the above described ultrasonic radiation procedure, the balloon 22 is deflated and shield 34 is collapsed over the particles trapped within it and the catheter 30 is withdrawn.

In FIG. 5, a catheter 40 is fed into artery 10 over a guide wire 18. Catheter 40 carries a balloon 22, an ultrasonic transducer 24, a second ultrasonic transducer 42 and a second balloon 44. Balloon 22 is placed in artery 10 within plaque deposits 12 and a thrombus 16. Energizing of ultrasonic transducer 24 operates as described above to cause dissolution of the thrombus 16 and to crack and soften the plaque deposit 12. Transducer 42 is for imaging as described above. Full inflation of the second balloon 44 blocks any flow downstream of itself and traps any large particles which result from ultrasonic irradiation of the plaque 12 and thrombus 16. A port 46 connected to an additional lumen (not shown) within catheter 40 is connected to a vacuum source which is operated to withdraw all the contents of the chamber between balloons 22 and 44 to the proximal end of catheter 40 and out of the artery 10. Following this, the balloons are deflated and catheter 40 is withdrawn from artery 10.

In some cases, the artery is substantially blocked by plaque deposits only. The balloon angioplasty process described above may be used to fracture and soften the plaque deposits. Alternatively, the process may have resulted in dissipating a thrombus. In either case, what remains is an artery whose internal wall is cracked and damaged, but with softened and fractured plaque remaining in the wall. This situation presents a consider able danger of migrating plaque particles or thrombus reforming at essentially the same location.

One way of treating the damaged artery 10 is as shown in FIG. 6. Assuming that one of the above processes has been completed, the catheter 20, 30 or 40 is removed and a new catheter 50 is inserted over guide wire 18 in which an intracoronary stent or sleeve 52 (typically of stainless steel) is placed over the balloon 54. Once located within the softened plaque deposit 12, the balloon 54 is inflated to a greater pressure than described above (up to 6–8 atmospheres) which causes stent 52 to become embedded in the artery wall, thereby closing off any cracks or fissures in the artery wall and eliminating the major source of thrombi.

Since time is often a concern with the above processes, another method is to place the stent over the balloon 22 at the outset. The process is then carried out as described in connection with FIGS. 2 and 3. Balloon 22 is then deflated permitting the material from thrombus 16 to be carried away after which the balloon 22 is again inflated to the higher pressure (up to 6–8 atmospheres) again forcing the stent 52 into the internal wall of the artery to seal off or close any cracks or fissures. A similar process can be used with the catheters of FIGS. 4 and 5 in which a similar stent can be placed over the balloon 22.

The above-described embodiments of the present invention are merely descriptive of its principles and are not to be considered limiting. The scope of the present invention instead shall be determined from the scope of the following claims including their equivalents.

I claim:

1. An angioplasty device for insertion into an artery having undesired deposits comprising:

an elongated flexible catheter having a proximal end, a distal end, and at least one lumen extending longitudinally therethrough:

first and second transducers at the distal end of said catheter and means for energizing said transducers;

a dilatation balloon at the distal end of said catheter surrounding at least one of said transducers and means for inflating said balloon such that when said one transducer is energized, energy from said transducer is transmitted through said balloon to said deposits;

said second ultrasonic transducer when energized providing images of said deposit;

a second balloon located on said catheter distal of said dilatation balloon;

a port positioned on said catheter between said dilatation balloon and said second balloon; and a lumen connected to said port and negative pressure means connected to said lumen.

2. An angioplasty device for insertion into an artery having an interior wall and deposits within said wall comprising:

an elongated flexible catheter having a proximal end, a distal end, and at least one lumen extending longitudinally therethrough;

an ultrasonic transducer on said catheter positioned to radiate ultrasonic energy radially in the region of said deposits;

a dilatation balloon surrounding said transducer such that when said transducer is energized, energy from said transducer is transmitted through said balloon to said deposits;

a second ultrasonic transducer secured to said catheter for providing images of said deposits;

a second balloon is carried on said catheter distal of said dilatation balloon, said balloons when inflated defining a chamber between said balloons; a port is located in said catheter between said balloons; and a lumen is connected to said port and to a source of negative pressure.

3. A method of treating an undesired deposit in a blood vessel through the use of a guidewire, a catheter on the guidewire having a proximal end and a distal end, a pair of ultrasonic transducers at the distal end of said catheter, and a dilatation balloon on said catheter surrounding at least one of said ultrasonic transducers, the steps of:

a) inserting said guidewire and catheter into said blood vessel until said balloon is adjacent said deposit;

b) inflating said balloon with a suitable liquid to cause the outside surface of said balloon to come into contact with said deposit;

c) energizing said one ultrasonic transducer to provide ultrasonic energy flowing through said liquid to impact on said deposit and cause ablation of said deposit;

d) energizing said second ultrasonic transducer to provide images of said deposit; and e) withdrawing said catheter, guidewire, balloon, and ultrasonic transducers from said blood vessel.

4. A method as claimed in claim 3 further comprising a stent carried coaxially on said balloon and following step d) said balloon is further inflated to install said stent in the wall of said blood vessel.

5. A method as claimed in claim 3 further comprising an expandable member secured to said catheter downstream of said dilatation balloon and following step b) said expandable member is expanded to substantially block said artery and following step d) said expandable member is collapsed against said catheter.

6. A method as claimed in claim 3 further comprising a second balloon located on said catheter distal of said dilatation balloon and a port in said catheter between said dilatation balloon and said second balloon wherein said second balloon is inflated essentially simultaneously with said dilatation balloon and following step c) ablated material between said balloons from said deposit is withdrawn through said port.

* * * * *